United States Patent
Luttermann et al.

(10) Patent No.: US 6,517,779 B1
(45) Date of Patent: Feb. 11, 2003

(54) DEVICE FOR SEPARATING MICRO OBJECTS

(75) Inventors: Klaus Luttermann, Neunkirchen-Seelscheid (DE); Edgar Diessel, Köln (DE); Markus Weidauer, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/214,839

(22) PCT Filed: Jul. 4, 1997

(86) PCT No.: PCT/EP97/03536
§ 371 (c)(1),
(2), (4) Date: Jan. 13, 1999

(87) PCT Pub. No.: WO98/03628
PCT Pub. Date: Jan. 29, 1998

(30) Foreign Application Priority Data

Jul. 19, 1996 (DE) .......................................... 196 29 143

(51) Int. Cl.[7] .............................. B01L 3/02; B01L 3/00; G01N 1/14; G01N 1/00; C12M 1/26
(52) U.S. Cl. ...................... 422/100; 422/99; 73/863.32; 73/863.83; 73/864; 73/864.01; 73/864.11; 73/864.31; 435/309.1
(58) Field of Search ................................ 422/100, 102, 422/99; 435/309.1; 73/864.11–864.31, 863.32, 864, 863.83, 864.01

(56) References Cited

U.S. PATENT DOCUMENTS

| | | | |
|---|---|---|---|
| 3,666,629 A | | 5/1972 | Moore |
| 4,199,013 A | * | 4/1980 | Reich et al. ............... 141/130 |
| 4,624,915 A | | 11/1986 | Schindler et al. .............. 435/4 |
| 4,695,709 A | * | 9/1987 | Sachs et al. ................ 219/494 |
| 4,707,337 A | * | 11/1987 | Jeffs et al. ................... 422/100 |
| 4,750,373 A | * | 6/1988 | Shapiro .................... 73/864.87 |
| 4,944,922 A | * | 7/1990 | Hayashi ....................... 422/100 |
| 4,956,297 A | | 9/1990 | Hood et al. .................. 435/810 |
| 5,141,131 A | * | 8/1992 | Miller, Jr. et al. ............. 222/54 |
| 5,211,805 A | | 5/1993 | Srinivasan ................... 156/643 |
| 5,456,880 A | * | 10/1995 | Miura ......................... 422/100 |
| 5,616,478 A | * | 4/1997 | Chetverin et al. ............. 435/91 |
| 5,658,727 A | * | 8/1997 | Barbas et al. ................... 435/6 |
| 5,705,813 A | * | 1/1998 | Appffel et al. ............... 250/288 |
| 5,770,158 A | * | 6/1998 | Eischen et al. .............. 422/100 |
| 5,866,350 A | * | 2/1999 | Canavaggio et al. .......... 435/13 |
| 6,204,030 B1 | * | 3/2001 | Liotta et al. ................. 435/100 |

FOREIGN PATENT DOCUMENTS

| | | |
|---|---|---|
| DE | 3204040 | 8/1983 |
| DE | 264705 | 2/1989 |
| DE | 4214430 | 11/1992 |
| DE | 4401076 | 7/1995 |
| DE | 4419638 | 12/1995 |
| GB | 2211111 | 6/1989 |
| JP | 1143647 | 6/1989 |

OTHER PUBLICATIONS

Patents Abstracts of Japan, Abstract of 3–240482 A., C–903, Jan. 22, 1999, vol. 16, No. 25.
Patents Abstracts of Japan, Abstract of 1–206986 A., C–654, Nov. 15, 1989, vol. 13, No. 510.

(List continued on next page.)

*Primary Examiner*—Lyle A. Alexander
*Assistant Examiner*—Brian R. Gordon
(74) *Attorney, Agent, or Firm*—Norris McLaughlin & Marcus

(57) ABSTRACT

The device serves for the transfer of microobjects, in particular of biological objects, from a current substrate (9) to a target substrate. In this case, use is made of a displaceable pipette system which is connected to a pressure generating device for aspirating in and flushing out the biological objects. The pipette system is disposed in a micromanipulator (3) and consists mainly of a substantially vertically disposed microcapillary (1) having a clear width of 1 $\mu$m to 50 $\mu$m.

6 Claims, 1 Drawing Sheet

OTHER PUBLICATIONS

Patents Abstracts of Japan, Abstract of 61–280265 A., C–421, May 8, 1987, vol. 11, No. 141.
Patents Abstracts of Japan, Abstract of 61–280264 A., C–421, May 8, 1987, vol. 11, No. 141.
Patents Abstracts of Japan, Abstract of 60–27377 A., C–287, Jun. 20, 1985, vol. 9, No. 145.
Patents Abstracts of Japan, Abstract of 59–78680 A., C–239, Aug. 23, 1984, vol. 8, No. 184.
Patents Abstracts of Japan, Abstract of 59–119739, C–220, Apr. 27, 1984, vol. 8, No. 93.
Benson, Jack A., *Electrophysiological Pharmacology of the Nicotinic and Muscarinic Cholinergic Responses of Isolated Neuronal Somata From Locust Thoracic Ganglia* J. Exp. Biol. 270, pp. 203–233(1992).
Schütze et al., *Catch and move—cut or fuse* Nature, vol. 368, (Apr. 14, 1994) pp. 667–669.

* cited by examiner

DEVICE FOR SEPARATING MICRO OBJECTS

The invention relates to a device for separating individual biological microobjects, in particular biological objects. In this case, the objects are disposed side by side on a fixed planar carrier. Using this method, individual objects can be spatially separated and isolated from a very large number of microobjects (e.g. $10^5$ to $10^6$). The prerequisite for this method of separation is the prior recognition and selection of the pertinent objects on the basis of significant analytical properties (e.g. by fluorescence spectroscopy or by radioactive labelling). "Microobjects" are understood dimension $\leq 50$ μm. Within the context of the present application, "biological objects" are understood as referring, above all, to (living) biological cells.

BACKGROUND OF THE INVENTION

The separation of biological cells using pipettes is in principle known. This involves methods which make use of pasteur pipettes. J. A. Benson, J. Exp. Biol. 170, 203 (1992) contains a description of the separation of cells of the order of magnitude between 50 and 100 μm, which are spatially separated out of a population using a pipette having a diameter of 0.5 mm.

To separate individual biological objects, objects are allowed to move in an aqueous solution using optical methods such as the optical tweezer (K. Schütze. A. Clement-Sengewald, Nature, 667 (Vol. 368) 1994). By reason of the low force transmission, this method is restricted to objects which can move freely in the solution. As the sorted objects as well as the unsorted objects are situated in the same solution, a separated cultivation can be achieved only with additional expenditure. For a separated cultivation, these cells must be separated by a different method, such as, for example, needling. Needles which are moved by micromanipulators and to which the cells adhere are also used as the sole method. In this case, the cells are directly contacted and could thus be mechanically stressed. In this case also, the manipulation is restricted to weakly adhering objects.

Separating or sorting apparatuses which are suitable for the separation of a large number ($>10^5$) of biological objects which are dispersed in a liquid are commercially available. While in the case of fluorescence-activated cell sorting (FACS=fluorescence activated cell sorter) electrostatic principles are used for the spatial separation, the magnetically activated cell sorter (MACS) operates by magnetic forces. In this case, however, the cells do not lie side by side on a planar carrier. In addition, both methods have the disadvantage that individual objects may be isolated only to a restricted extent (FACS) or may not be isolated at all separately from one another (MACS).

Furthermore, methods are known under the name "Ablative Photodecomposition", in which methods a controlled removal of material in the case of polymers takes place using pulsed UV lasers, in particular using excimer lasers. These methods may be regarded as etching methods in the broadest sense. A similar method, in which, however, a continuously operated UV laser is used, is described in U.S. Pat. No. 5,211,805. This method is intended to be suitable for the industrial processing of technical polymers and for the biomedical treatment of biological tissue. In this case, use is made of a sorting principle which, using laser beams, destroys the undesired biological objects situated on a carrier by means of high radiation doses, while the selected (desired) objects remain (U.S. Pat. No. 4,624,915). This process is relatively costly, when applied to the selection of individual objects from large populations.

SUMMARY OF THE INVENTION

The object underlying the invention resides in the spatial separation of individual microobjects, in particular of known biological cells, which are laid out side by side, with a high occupation density, on a planar carrier and adhere to this carrier. In this case, the survivability of the biological objects is as a rule to remain preserved; that is to say the biological objects are not to be damaged or impaired by the separation process.

Proceeding from a device having a displaceable pipette system which is connected to a pressure generating device for aspirating in and flushing out the biological objects, this object is achieved according to the invention in that the pipette system is disposed in a micromanipulator and has a substantially vertically disposed microcapillary having a clear width of 1 μm to 50 μm, preferably 5 μm to 20 μm.

DETAILED DESCRIPTION

In this case, "substantially vertically" means that a deviation of ±20° can be permitted. In this instance, in the simplest case a pump or piston syringe serves as pressure generating device.

Preferably, the microcapillary consists of a cylindrical glass tube and is advantageously bent over at a right angle. In this case, a deviation from the right angle by approximately ±20° can likewise be accepted.

In order to implement various aperture diameters with the same outlet diameter of the capillaries in the production process in non-problematic fashion, capillaries are used which are made of different materials, such as borosilicate glass, aluminium silicate glass or haematocrit glass.

A particularly preferred embodiment of the invention is characterized in that the micromanipulator and the pump are controlled in such a way that in the event of a reduced pressure setting in one working step a plurality of biological objects are aspirated in, in succession, by the microcapillary and subsequently, in the next working step, are flushed out again, in succession, with an excess pressure setting.

With regard to the transfer of bacteria, the current substrate and the target substrate expediently consist of a carrier coated with agar or agarose.

Alternatively, however, a microtitration plate can also be used as target substrate.

In the text which follows, the invention is explained in greater detail with reference to an illustrative embodiment shown in the drawing. The drawing shows the basic structure of the transfer device at a microscope workstation. The device according to the invention can be used for the separation of microobjects such as for example of polymer beads within the context of combinatorial chemistry or of bacteria within the context of molecular biology. By way of example, in this instance the use of the device for the sorting of bacteria is described.

For the transfer of the bacteria, use is made of microcapillaries of a special glass which are produced by means of a drawing process in the molten condition. For the experiments to be described, small borosilicate glass tubes (company Hilgenberg, Malsfeld, GER) having an outlet diameter of 1.6 mm were used. In a three-stage drawing process using a commercially conventional pipette drawing system (DMZ universal puller, company Zeitz-Instrumente, Munich, GER), capillaries were produced having a pipette form which is cylindrical in the end region of the capillary (i.e. not as otherwise conventional, drawn out to a tapering tip!) having an aperture diameter of approximately 6 μm at the fused end. On the other side, the outlet diameter is preserved in unchanged condition. This pipette form has proved to be effective for the purposes of the reproducibility of the transfer process, in particular of the flushing-out process. Alternatively, the capillary can also be produced from an aluminium silicate glass or haematocrit glass.

BRIEF DESCRIPTION OF THE DRAWINGS

The apparatus for the transfer process is diagrammatically represented in the drawing. The microcapillary 1 is held in a clamping gripper 2, which is mounted on the micromanipulator 3, which permits a three-dimensional positioning within the μm range. Such manipulators are commercially available. The microcapillary 1 is connected via a hose 4 to a commercially conventional piston syringe 5, with the aid of which the capillary internal pressure is set. The pressure is determined by means of a pressure gauge 6. Both the micromanipulator 3 and the syringe 5 are remotely controlled by means of stepping motors, which are not shown here. The entire procedure of the aspirating-in and the separation of a bacteria, (picking process) is subject to the visual inspection which is made possible by observation with a 40-fold magnification in phase contrast. Only the objective 7 and the illumination condenser 8 of the microscope are shown here. With regard to the required operating spacing of the condenser 8 of approximately 22 mm from the object, the microcapillary 1 is heated beyond the softening point and bent over in such a way that it forms almost a 90° angle and can thus be positioned in space-saving fashion below the condenser 8. In this way, the observation of the transfer process can take place without disturbance. For the high spatial resolution of the transfer process of the order of magnitude of the pipette diameter (in this case 6 μm), it is important that the pipette impinges perpendicularly on the object to be picked. In this case, a deviation of a maximum of ±20° can be tolerated. In this way, no water film which could adversely affect surrounding objects in the course of the transfer process is formed between capillary wall and agar substrate. To prepare for picking, a buffer solution is drawn into the capillary 1 from the storage vessel, applying a reduced pressure. In this case, it is sufficient that only the tapered part of the capillary is filled with the buffer solution.

Now, the object to be picked or the bacterium 10 to be separated from the substrate 9 is positioned by means of a coordinate-controlled movement of the microscope displaceable stage below the capillary 1. In this case, the capillary internal pressure is set to −300 mbar as compared with ambient pressure. With simultaneous microscope observation, the capillary 1 is placed directly over the bacterium 10 to be picked onto the agarose substrate 9. Subsequently, the microcapillary 1 is raised by means of the height adjustment on the micromanipulator 3 and, as a result, the empty substrate surface remains behind in the microscope image. To flush out the bacterium 10, either the microcapillary 1 or the displaceable stage is run to an appropriate position on the target substrate. In this case, the internal pressure is increased to +100 mbar. While the capillary 1 is being placed onto the target substrate (in this case the marginal zone (11) on the substrate 9), the flushing-out process takes place. After capillary 1 has been raised again from the target substrate, the flushed-out bacterium again becomes visible in the phase contrast image of the microscope. In this way, in four examples, in each case 10 bacteria were transferred from an initial substrate to a target substrate which contained nutrient medium. After a growing time of a few days, colonies of the individual bacteria were formed in 50–60% of the cases. In a test of the vitality rate of the initial population a value of 60% was determined, so that on this basis the transfer process can be regarded as very mild. Alternatively, the bacteria can be added to a liquid, e.g. PBS buffer. This liquid can be simulated in the wells of commercially conventional 96 or 384 microtitration plates.

Figure 1:
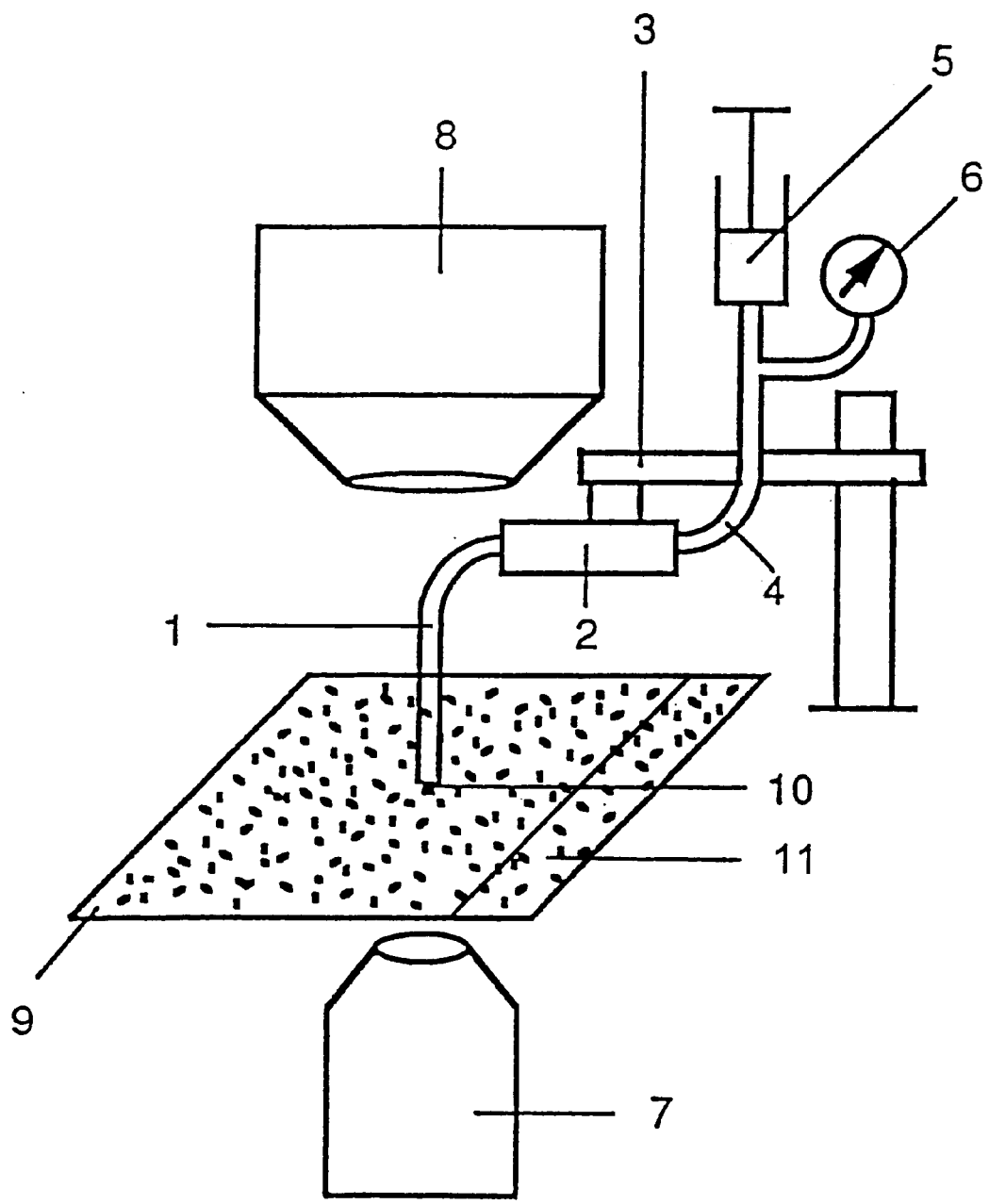

Besides the picking and flushing-out processes taking place directly one after the other, a plurality of bacteria were also picked successively in one working step and, in corresponding succession, flushed out again on the target substrate. For this purpose, the micromanipulator 3 and the syringe 5 are controlled in such a way that with a constant reduced pressure setting, individual bacteria are picked up in succession. In this case, the bacteria are drawn in, in that the capillary 1 is lowered in succession onto the substrate positions which carry the bacterium to be picked. Subsequently, with a constant excess pressure setting, the bacteria are flushed out, in that the capillary is lowered in succession onto various positions of the substrate.

This procedure is relatively time-saving, since the paths between the objects to be sorted can be optimized and also the pressure setting in the capillary needs to be undertaken only once in each instance. The advantage in the use of bacteria resides in the simple amplification by regular growth. In addition, with the aid of the Polymerase Chain Reaction (PCR) it is possible to amplify from individually sorted bacteria the gene sequences which are responsible for the specific property of the bacteria.

What is claimed is:

1. A device for the transfer of microobjects from a current substrate to a target substrate, having a displaceable pipette system which is connected to a pressure generating device for aspirating in and flushing out the microobjects, wherein the pipette system is disposed in a micromanipulator and has a microcapillary having a first end which is open to receive and discharge said microobjects, which first end has a clear width of 1 μm to 50 μm, a distal end of the microcapillary beingdisposed substantially vertically, and a medial portion of the microcapillary of adjacent the distal end being disposed substantially at a right angle to the distal end, the microcapillary having a fixed shape.

2. The device according to claim 1, wherein the microcapillary consists of a cylindrical glass tube.

3. The device according to claim 1, wherein the microcapillary consists of borosilicate glass, aluminum silicate glass or haematocrit glass.

4. Device according to claim 1, further comprising means controlling the micromanipulator and the pressure generating device in such a way that in the event of a reduced pressure setting in one working step a plurality of biological objects are aspirated in, in succession, by the microcapillary and subsequently, in the next working step, are flushed out again, in succession with an excess pressure setting.

5. The device according to claim 1, wherein the current substrate and the target substrate consist of a carrier coated with agar or agarose.

6. The device according to claim 1, wherein the target substrate consists of a microtitration plate.

* * * * *

UNITED STATES PATENT AND TRADEMARK OFFICE
CERTIFICATE OF CORRECTION

PATENT NO. : 6,517,779 B1
DATED : February 11, 2003
INVENTOR(S) : Klaus Luttermann et al.

It is certified that error appears in the above-identified patent and that said Letters Patent is hereby corrected as shown below:

Column 4,
Line 44, delete "beingdisposed" and insert -- being disposed --
Line 45, delete "of" after "microcapillary"

Signed and Sealed this

Twenty-second Day of April, 2003

JAMES E. ROGAN
*Director of the United States Patent and Trademark Office*